United States Patent [19]

Holtkamp, Sr.

[11] Patent Number: Plant 7,330

[45] Date of Patent: Sep. 18, 1990

[54] AFRICAN VIOLET PLANT NAMED IMPROVED SOUTH CAROLINA

[76] Inventor: Reinhold Holtkamp, Sr., Blumenstrasse 28, D 4242 Rees-Haffen, Fed. Rep. of Germany

[21] Appl. No.: 363,464

[22] Filed: Jun. 8, 1989

[51] Int. Cl.[5] ..... A01H 5/00
[52] U.S. Cl. ..... Plt./69
[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Improved South Carolina characterized by its shiny white, star-shaped flowers with slightly wavey edges; occasional purplish blue touch in the center; strong, upright flower stems that curve slightly toward the center to form a compact bouquet above the leaves; medium green, oval, slightly serrated leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Improved South Carolina.

The new cultivar was referred to during the breeding and selection process by the designation 6/19 J. M. and is a product of a planned breeding program. The basic objective of the breeding program was to create a new African violet cultivar improving certain characteristics of the cultivar South Carolina, disclosed in my U.S. Plant Pat. No. 4,777. The new cultivar was originated from a cross made by me in the controlled breeding program in Haffen, Federal Republic of Germany. The female, or seed parent was a cultivar designated XXI/3. The male, or pollen parent was a cultivar designated 4158.

Improved South Carolina was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Improved South Carolina has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice.

The following traits have been repeatedly observed and are determined to be basic characteristics of Improved South Carolina, which in combination distinguish this African violet as a new and distinct cultivar:

(1) Strong, upright flower stems curving slightly toward the center.

(2) White, star-shaped flowers with somewhat wavy edges and an occasional purplish blue touch in the center.

(3) Each plant carries 8–10 and more upright flower stems each of which carries 8–10 and more flowers.

(4) Long lasting, non-dropping flowers.

(5) Vigorous and compact grower.

(6) Plant saleable 10 to 11 weeks after potting.

(7) Seed capsules push slightly through.

(8) Medium green, oval leaves.

(9) After maturity the flowers dry off, and remain on the peduncle without becoming infected by botrytis.

The new cultivar is most similar to, and was specifically intended to improve upon the characteristics of, my previously patented cultivar South Carolina. In comparison to South Carolina, the new cultivar is principally distinguished by its smaller leaves, more compact growth habit, somewhat smaller blooms, occasional purplish blue touch in the center, and better flowering habit.

The accompanying color photograph drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn.

Botanical classification: *Saintpaulia ionantha,* Ramat., c.v. Improved South Carolina.

Parentage:

*Male parent.*—4158.

*Female parent.*—XXI/3.

Propagation: The new cultivar holds its distinguishing characteristics through successive propagations by leaf cuttings.

Plant: From 8 cm to 11 cm tall when grown in pots, and approximately 24–27 cm in diameter when fully grown.

*Leaves.*—General form: Oval. Diameter: 50–60 mm wide and 65–70 mm long. Texture: Leatherlike. Aspect: Hairy, slightly shiny, slightly serrated. Veins: Upperside: Well visible; underside: Well pronounced, light green, shiny. Color (upperside): Yellow-Green Group 147 A. Color (underside): Greyed-Green Group 194 C. Petiole: Strong upright, light green, hairy.

*Flowers.*—Buds: Bell-shaped, 8–9 mm just before opening, greenish white. Sepals: Five (5). Color: Green. Calyx: Shape: Funnel-shaped. Aspect: Spear-shaped, hairy. Peduncle: Character: Strong upright, hairy. Color: Green. Individual flowers: Size: 40–43 mm. Shape: Star-shaped with wavy edges. Color (upperside): White with an occasional touch of Violet Group 88 B to C in the center of some blooms. Color (underside): White. Borne: Each flower stem carries 8–10 and more flowers on strong, upright peduncle that are free standing above the leaves, thereby forming a compact bouquet. Flowering habit: Flowers 10–11 weeks after potting.

*Reproductive organs.*—Stamens: Five (5). Anthers: 5 composed of 10 anther cells, seed capsule pushes slightly through. Filaments: Yellowish green, 3–4 mm long. Pollen color: Yellow Group 7 A. Styles: 6 mm long, purplish, base of ovary light green and hairy.

*Roots.*—Normally developed, white when young, turning slightly brownish when older.

Disease resistance: Good.

General observations: Improved South Carolina is a very attractive, vigorous and compact grower with medium green, oval, slightly serrated leaves. A tight bouquet of flowers free standing above the leaves develops after approximately 10–11 weeks. Each of the 8–10 and more strong flower stems carries 8–10 and more shiny white, star-shaped flowers with slightly wave edges. Occasionally, the center of some blooms may have a purplish blue touch. The flowers are long-lasting and non-dropping and the seed capsules push slightly through. Occasionally, an additional small petal may develop in the center.

I claim:

1. A new and distinct cultivar of African violet named Improved South Carolina, as described and illustrated, and particularly characterized by its shiny white, star-shaped flowers with slightly wavy edges; occasional purplish blue touch in the center; strong, upright flower stems that curve slightly toward the center to form a compact bouquet above the leaves; medium green, oval, slightly serrated leaves; profuse flowering, vigorous and compact growth habit, flowering 10–11 weeks after potting, and its long lasting and non-dropping flowers.

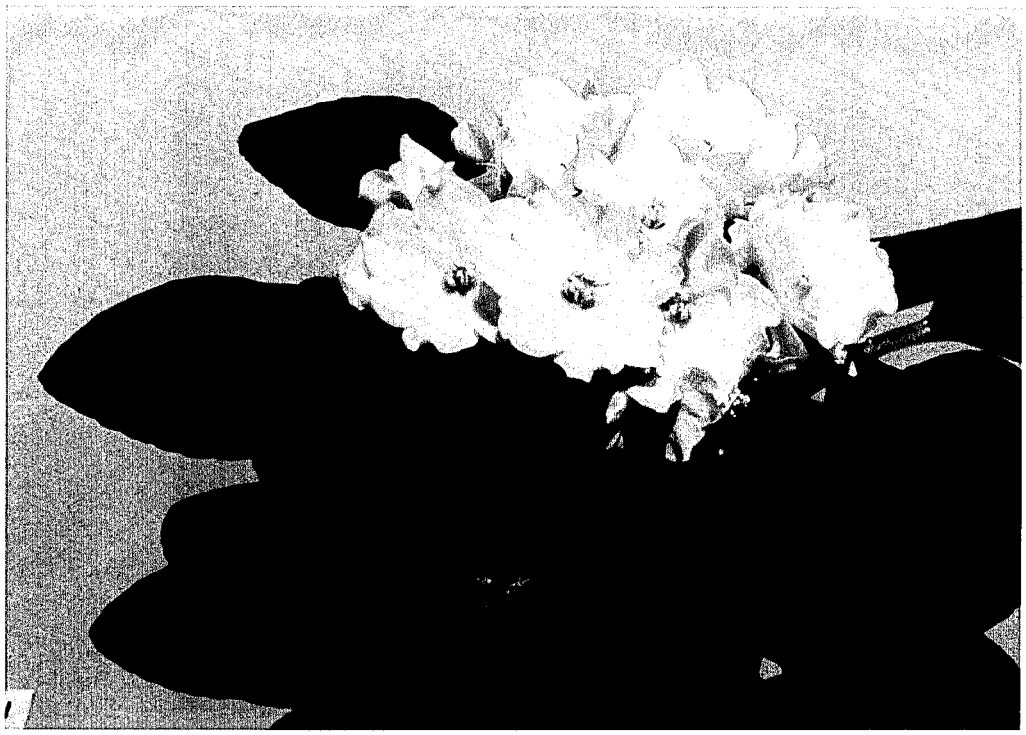

* * * * *